(12) United States Patent
Han et al.

(10) Patent No.: US 10,925,563 B2
(45) Date of Patent: Feb. 23, 2021

(54) X-RAY IMAGING APPARATUS

(71) Applicant: SAMSUNG ELECTRONICS CO., LTD., Suwon-si (KR)

(72) Inventors: Dae Woong Han, Suwon-si (KR); Seung Hwan Lee, Yongin-si (KR); Jin Woo Lee, Suwon-si (KR); N. V. Deepak, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/468,126

(22) PCT Filed: Nov. 30, 2017

(86) PCT No.: PCT/KR2017/013894
§ 371 (c)(1),
(2) Date: Jun. 10, 2019

(87) PCT Pub. No.: WO2018/105948
PCT Pub. Date: Jun. 14, 2018

(65) Prior Publication Data
US 2020/0069269 A1 Mar. 5, 2020

(30) Foreign Application Priority Data

Dec. 9, 2016 (KR) .................. 10-2016-0168035
Nov. 27, 2017 (KR) .................. 10-2017-0159263

(51) Int. Cl.
*A61B 6/00* (2006.01)
*G01N 23/04* (2018.01)

(52) U.S. Cl.
CPC ............ *A61B 6/447* (2013.01); *A61B 6/4405* (2013.01); *G01N 23/04* (2013.01); *G01N 2223/301* (2013.01); *G01N 2223/308* (2013.01)

(58) Field of Classification Search
CPC ...................................................... A61B 6/447
See application file for complete search history.

(56) References Cited

U.S. PATENT DOCUMENTS

| | | | |
|---|---|---|---|
| 2011/0249807 A1* | 10/2011 | Dirisio | A61B 6/447 378/198 |
| 2014/0098942 A1* | 4/2014 | Omura | H05G 1/02 378/197 |
| 2016/0199013 A1* | 7/2016 | Moreno Vallejo | A61B 6/4405 378/194 |

FOREIGN PATENT DOCUMENTS

| | | |
|---|---|---|
| CN | 203852364 U | 10/2014 |
| JP | 2000-23958 | 1/2000 |

(Continued)

OTHER PUBLICATIONS

International Search Report, PCT/ISA/210 dated Feb. 9, 2018 in corresponding International Application No. PCT/KR2017/013894.

(Continued)

*Primary Examiner* — Hoon K Song
(74) *Attorney, Agent, or Firm* — Staas & Halsey LLP

(57) ABSTRACT

The present disclosure relates to an X-ray imaging apparatus. The X-ray imaging apparatus includes a first column connected to a main body, a second column connected to the first column and provided to be movable relative to the first column, an arm connected to the second column and slidably provided along the second column, and a weight compensator provided to compensate for the weight of the second column and the arm, wherein the weight compensator, the second column and the arm are connected by a wire, and the second column is provided with an elastic member connected to the arm and providing an elastic force such that the arm is moved by a uniform force regardless of the position of the second column.

10 Claims, 14 Drawing Sheets

(56) References Cited

FOREIGN PATENT DOCUMENTS

| JP | 2013-523400 | 6/2013 |
|----|-------------|--------|
| JP | 2015-54200 | 3/2015 |
| KR | 10-2016-0030028 | 3/2016 |

OTHER PUBLICATIONS

PCT/ISA/237dated Feb. 9, 2018 in corresponding International Application No. PCT/KR2017/013894.

* cited by examiner

X-RAY IMAGING APPARATUS

CROSS REFERENCE TO RELATED APPLICATIONS

This application is a National Phase application, under U.S.C. § 371, of International Application No. PCT/KR2017/013894 filed Nov. 30, 2017, which claims priority to Korean Patent Application No. 10-2017-0159263, filed Nov. 27, 2017 and Korean Patent Application No. 10-2016-0168035, filed Dec. 9, 2016, the entire disclosures of which are herein incorporated by reference as a part of this application.

TECHNICAL FIELD

The present disclosure relates to a mobile X-ray imaging apparatus.

BACKGROUND ART

An X-ray imaging apparatus is an apparatus for obtaining an image of the inside of an object using an X-ray. The X-ray imaging apparatus may image the inside of the object in a non-invasive manner by irradiating the object with X-rays and detecting the X-rays transmitted through the object. The medical X-ray imaging apparatus may be used for diagnosis of injury or illness inside the object which not be confirmed by appearance.

A typical X-ray imaging apparatus has an X-ray source and an X-ray detector fixed in a certain space, and thus in order to take an X-ray, a patient must move to the laboratory where the X-ray imaging apparatus is located and move the body according to the apparatus.

However, in the case of a patient having difficulty in moving, it is difficult to take an X-ray with a general x-ray imaging apparatus, and therefore a mobile X-ray imaging apparatus capable of taking an X-ray regardless of a place has been developed.

Because the mobile X-ray imaging apparatus is equipped with an X-ray source on a movable body and uses a portable X-ray detector, it is possible to perform X-ray shooting by directly visiting a patient who is inconvenient to move.

DISCLOSURE

Technical Problem

The present disclosure is directed to providing an X-ray imaging apparatus provided to extend or retract a column for mounting an X-ray source.

Further, the present disclosure is directed to providing an X-ray imaging apparatus capable of reducing the weight of the column provided to be extended or retracted.

Technical Solution

One aspect of the present disclosure provides an X-ray imaging apparatus including a first column connected to a main body, a second column connected to the first column and provided to be movable relative to the first column, an arm connected to the second column and slidably provided along the second column, and a weight compensator provided to compensate for the weight of the second column and the arm, wherein the weight compensator, the second column and the arm are connected by a wire, and the second column is provided with an elastic member connected to the arm and providing an elastic force such that the arm is moved by a uniform force regardless of the position of the second column.

The wire connecting the weight compensator, the second column and the arm may be provided in a single unit.

The elastic member may be a static-load elastic member.

The elastic member may be a static-torque elastic member.

The weight compensator may include a spring balancer to which the wire is connected and that is provided to compensate for the weight of the second column and the arm.

The weight compensator may further include a guide pulley to which the wire is connected, and the spring balancer may compensate for the load of the second column and the arm with a uniform force by the guide pulley.

The second column may be provided with a column brake capable of braking the movement of the second column.

The second column may be provided with an arm brake capable of braking the movement of the arm.

The first column may be provided with a first sensor capable of sensing the second column.

The first sensor may be provided to sense the second column when the second column is located at a lowermost portion to which the second column is movable at the lowermost in the first column.

The second column may be provided with a second sensor capable of sensing the arm.

The second sensor may be provided to sense the arm when the arm is located at an uppermost portion to which the arm is movable at the uppermost in the second column.

Another aspect of the present disclosure provides an X-ray imaging apparatus including a first column connected to a main body, a second column connected to the first column and provided to be movable relative to the first column, an arm connected to the second column and slidably provided along the second column, a first weight compensator including a first spring balancer to compensate for the weight of the second column and the arm, and a second weight compensator provided in the second column and including a second spring balancer to compensate for the weight of the arm, wherein the first weight compensator includes a first wire to connect the second column and the first spring balancer, and the second weight compensator includes a second wire to connect the arm and the second spring balancer.

Another aspect of the present disclosure provides an X-ray imaging apparatus including an arm on which an X-ray source is mounted, a first column on which the arm is slidably mounted, a second column on which the first column is mounted to be relatively movable, a first weight compensator provided in the second column to compensate for the weight of the first column and the arm, and a second weight compensator provided in the first column to compensate for the weight of the arm, wherein the first weight compensator includes a hydraulic spring to support the load of the first column and the arm.

The first weight compensator may include a driving source and a connector to connect the driving source and the second column, and the connector may support the load of the first column and the arm by receiving a driving force from the driving source.

The first column may be provided with a support extending from first column, and the hydraulic spring may support the bottom surface of the support.

The second weight compensator may include a ball screw and a nut portion to move along the ball screw.

The arm may be mounted to the nut portion.

The second weight compensator may include a driving source, and the ball screw may be rotated by receiving a driving force from the driving source.

Advantageous Effects

An X-ray imaging apparatus according to an embodiment can adjust the position of an X-ray source variously, so that an X-ray image can be shot at various angles and ranges.

Further, a column on which the X-ray source is mounted can be extended or retracted, so that a user's field of view can be secured when the X-ray imaging apparatus is moved.

Further, the column provided in the X-ray imaging apparatus can be lightened, so that the X-ray imaging apparatus can be easily moved.

MODE OF THE INVENTION

Hereinafter, an X-ray imaging apparatus according to an embodiment will be described in detail with reference to the drawings.

Figure 1:
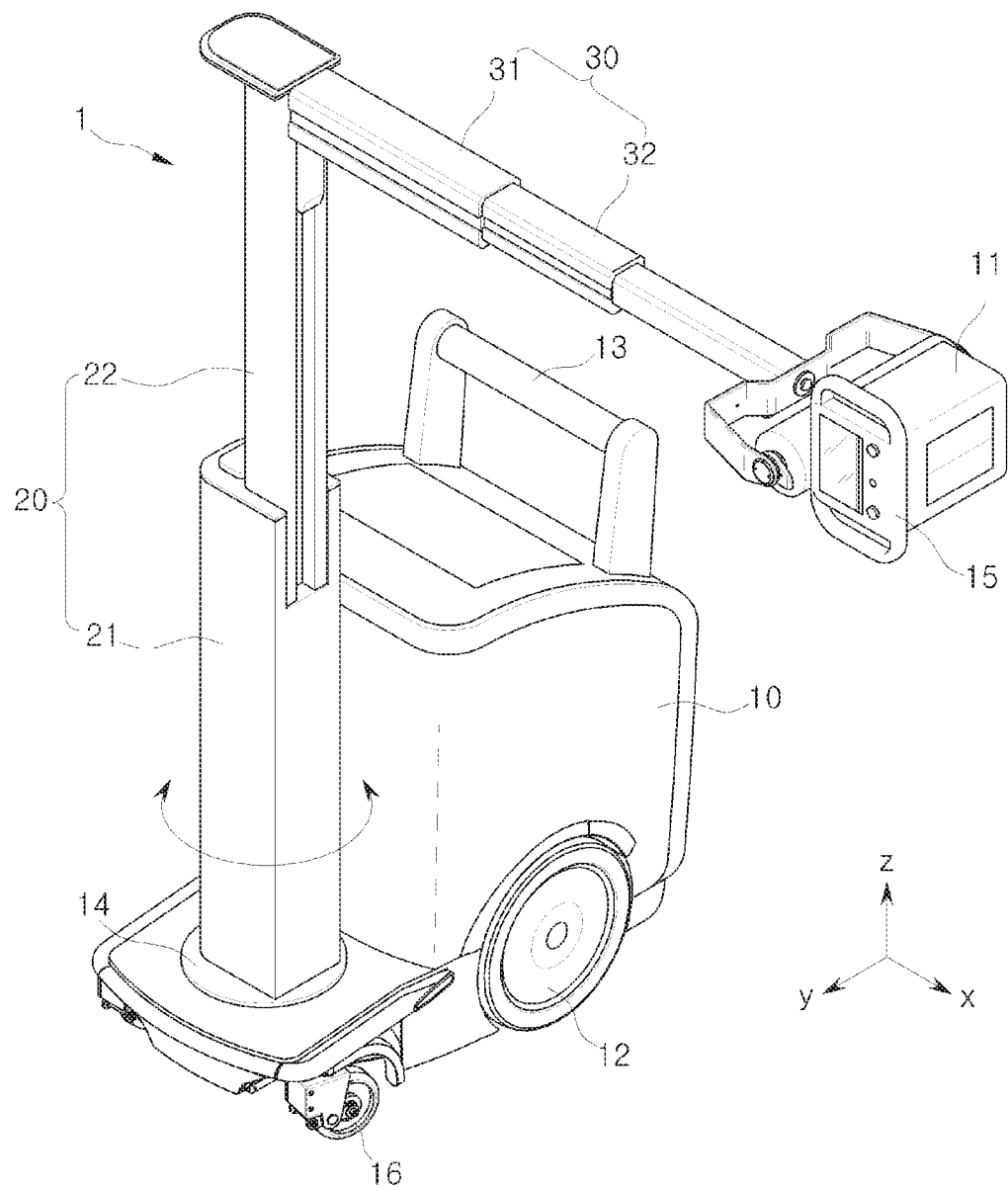
FIG. 1 is a perspective view of an X-ray imaging apparatus according to an embodiment.
Figure 2:
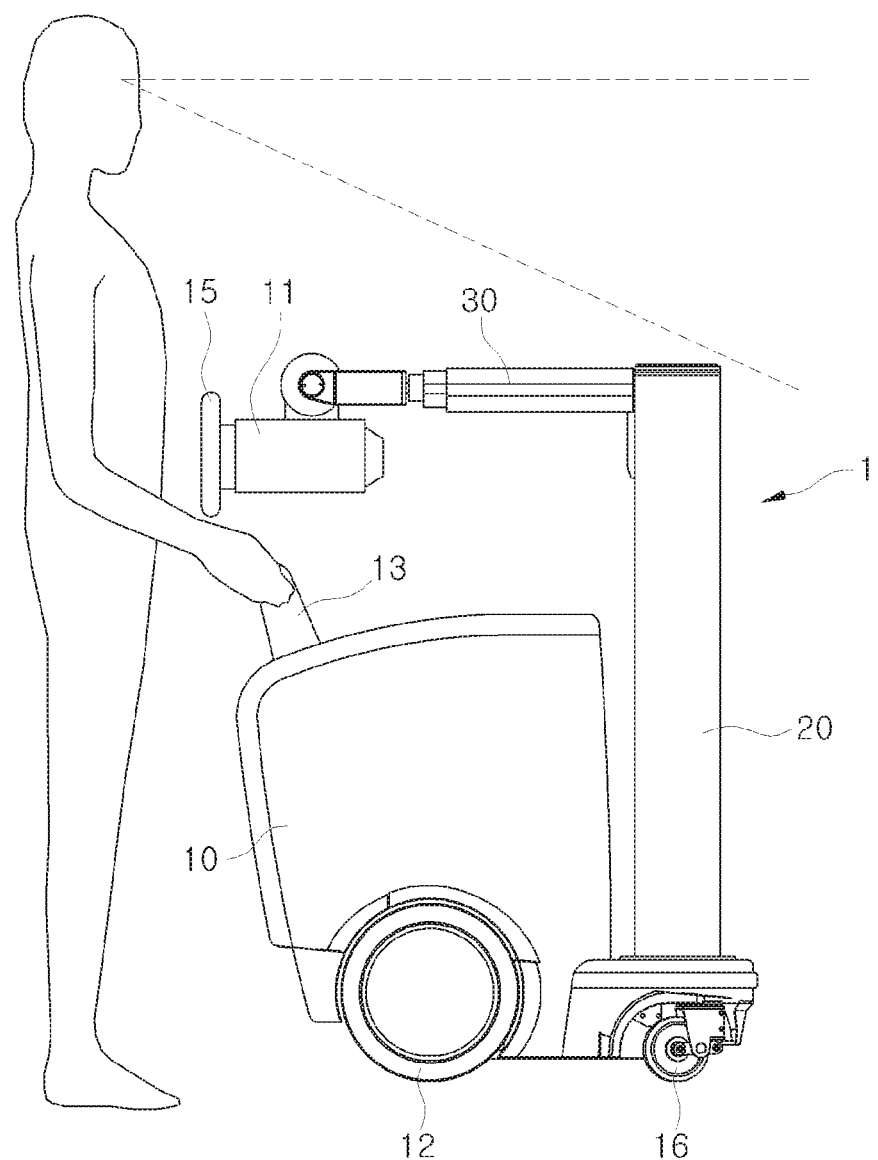
FIG. 2 is a side view of the X-ray imaging apparatus according to an embodiment.
Figure 3A:
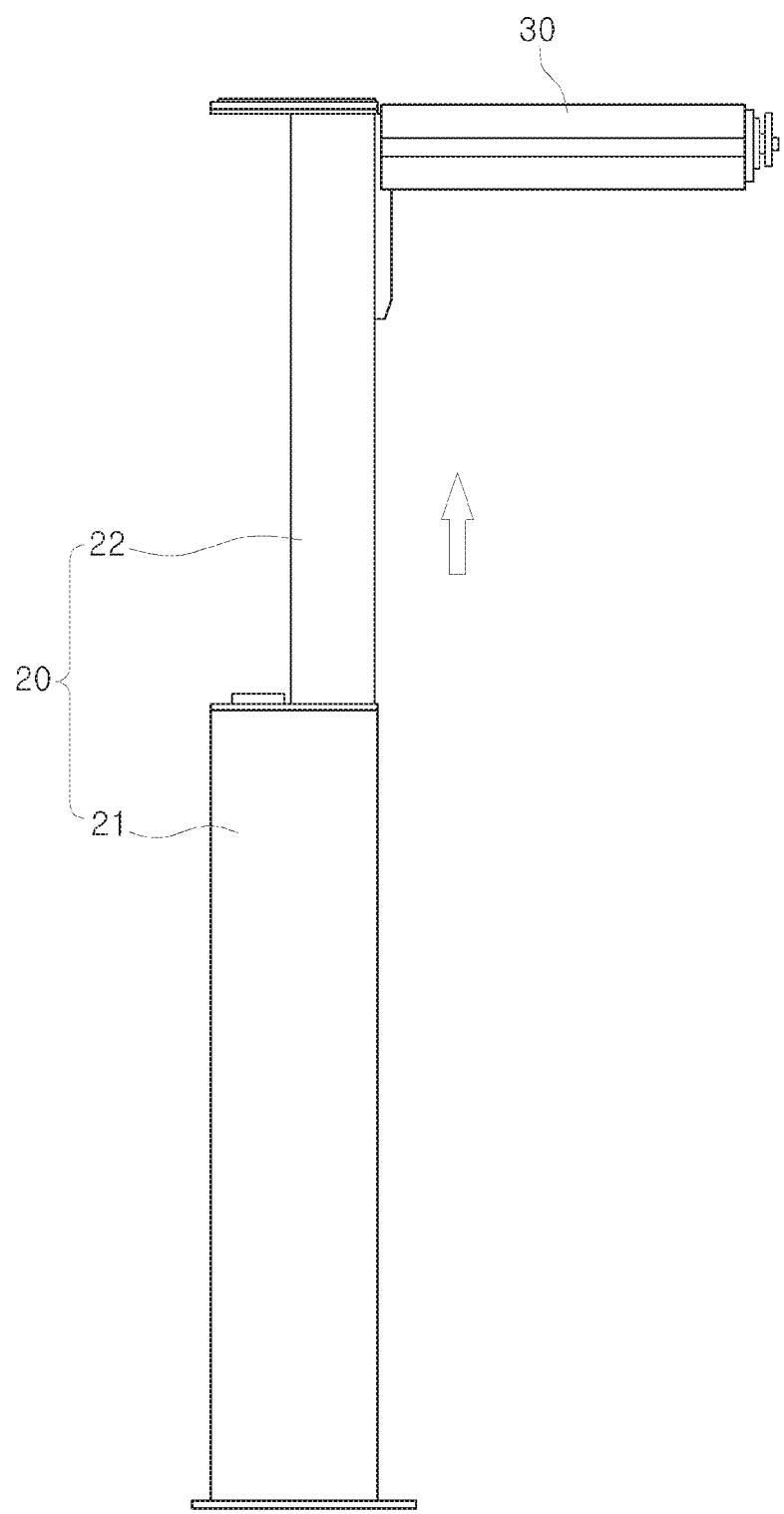
FIGS. 3A to 3C are views illustrating a column of the X-ray imaging apparatus according to an embodiment.
Figure 3B:
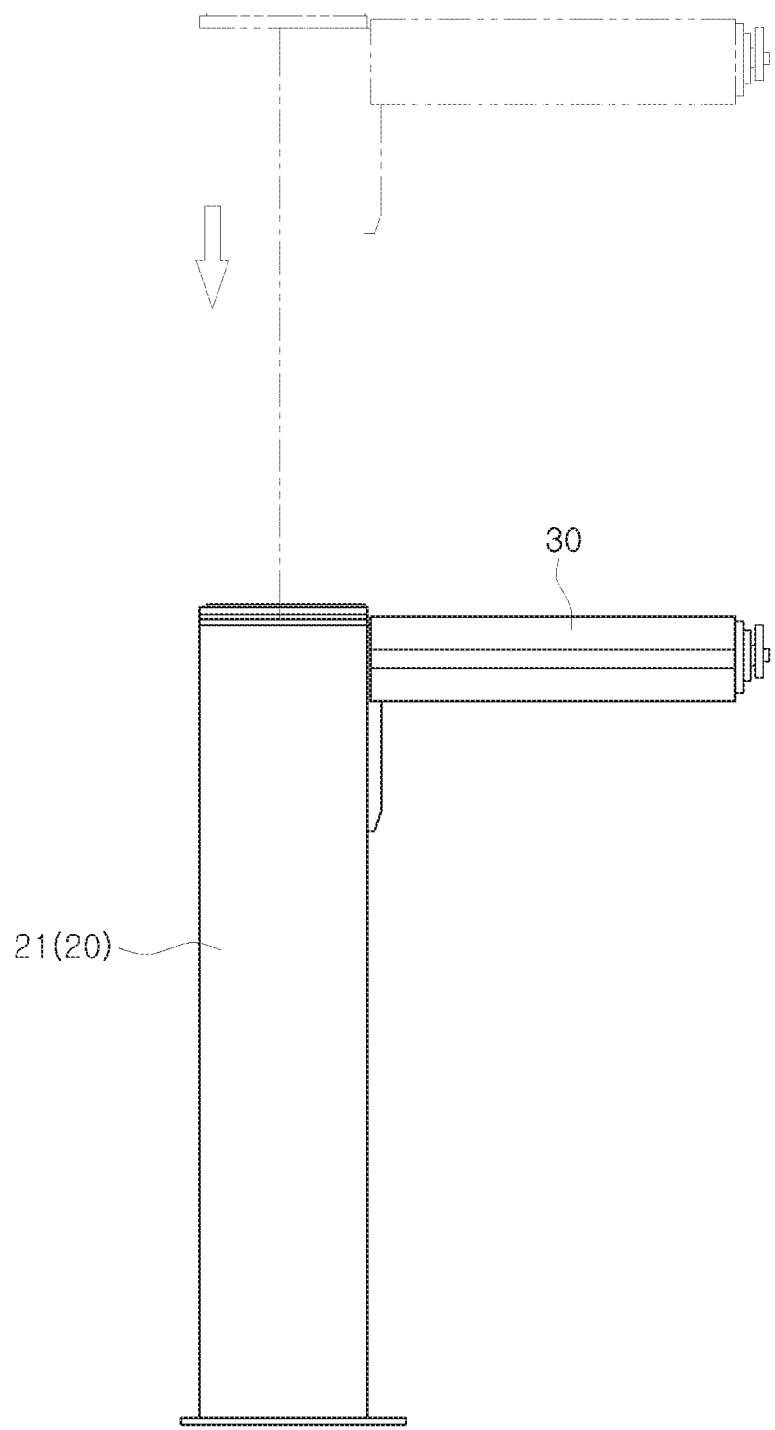
Figure 3C:
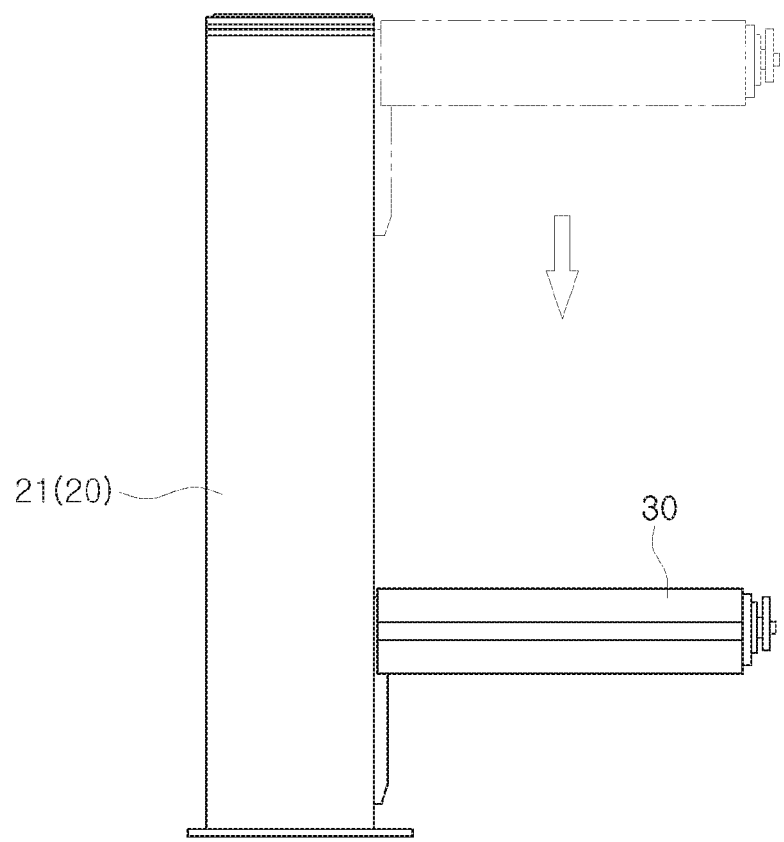

FIG. 1 is a perspective view of an X-ray imaging apparatus according to an embodiment, FIG. 2 is a side view of the X-ray imaging apparatus according to an embodiment, and FIGS. 3A to 3C are views illustrating a column of the X-ray imaging apparatus according to an embodiment.

Referring to FIGS. 1 to 3C, an X-ray imaging apparatus 1 according to an embodiment may include a main body 10 and an X-ray source 11 mounted on the main body 10. The main body 10 may be movably provided by a wheel 12. The main body 10 may further include casters 16. It is possible to easily change the direction of the X-ray imaging apparatus 1 when the X-ray imaging apparatus 1 is moved by the casters 16 which are rotatably provided in all directions.

The main body 10 is provided with a handle 13 so that a user may hold the handle 13 and push or pull the main body 10 to move the main body 10. The main body 10 may be provided with a control panel 15. The user may control the operation of the X-ray imaging apparatus 1 by operating the control panel 15.

The main body 10 may be provided with a column 20 whose length may be varied. The main body 10 may be rotatably provided with a rotary panel 14 and the column 20 may be mounted on the rotary panel 14. The column 20 may rotate together with the rotary panel 14. As the column 20 rotates, the x-ray source 11 connected to the column 20 rotates and its position may be varied. As such, the position of the X-ray source 11 is variable, so that X-ray shooting may be performed at various angles.

The column 20 may include a first column 21 and a second column 22 provided to be capable of extending from the first column 21. The second column 22 may be provided to be slidable along the first column 21. The length of the column 20 may increase when the second column 22 slides upward along the first column 21, and the length of the column 20 may decrease when the second column 22 slides downward along the first column 21.

An arm 30 to which the X-ray source 11 is mounted may be mounted to the second column 22. The arm 30 may be provided to be slidable along the second column 22. The position of the X-ray source 11 in a vertical direction may be varied by sliding the arm 30 along the second column 22.

The arm 30 may be provided to be extendable. As the arm 30 is extended or retracted, the X-ray source 11 mounted on an end of the arm 30 moves laterally so that the position thereof may be varied.

As an example, the arm 30 may include a first arm 31 mounted on the second column 22 to be slidable along the second column 22, and a second arm 32 provided to be extendable from the first arm 31. The X-ray source 11 may be mounted on an end of the second arm 32. The length of the arm 30 may increase or decrease by sliding the second arm 32 in the one direction or the other direction from the first arm 31. The configuration of the arm 30 is not limited to that described above.

When the X-ray imaging apparatus 1 is moved by the user, the column 20 and the arm 30 may be shortened in length to secure the user's field of view and prevent collision with obstacles. The second column 22 is positioned to overlap the first column 21 and the second arm 22 is positioned to overlap the first arm 21 so that the length of the column 20 and the length of the arm 30 may be minimized. The X-ray source 11 mounted to the arm 30 may be positioned at an upper portion of the main body 10 to avoid impact with an external obstacle.

When the X-ray imaging apparatus 1 is moved, the length of the column 20 and the arm 30 may be shortened so that the X-ray imaging apparatus 1 may be safely moved. When an X-ray image is shot by the X-ray imaging apparatus 1, the lengths of the column 20 and the arm 30 may be extended so that the position of the X-ray source 11 may be varied to facilitate the X-ray shooting.

A conventional X-ray imaging apparatus is provided with a separate driving source for extending or retracting a column. The conventional X-ray imaging apparatus has a disadvantage in that the X-ray source may not be positioned at a desired position within a short time because the column may not move quickly when moving by receiving the driving force from the driving source.

As another example, a conventional X-ray imaging apparatus may manually increase or decrease the length of a column. In this case, a weight or the like is used to compensate the weight of a second column and an arm mounted on the second column so that the second column may be moved with a small force. In a case where the weight is compensated for by a weight or the like, the weight of the X-ray imaging apparatus may increase and the mobility may decrease.

The present disclosure discloses an X-ray imaging apparatus capable of increasing or decreasing the length of a column manually without including a separate driving source or a weight or the like. Hereinafter, the internal structure of the column capable of manually increasing or decreasing the length of the column will be described.

Figure 4:
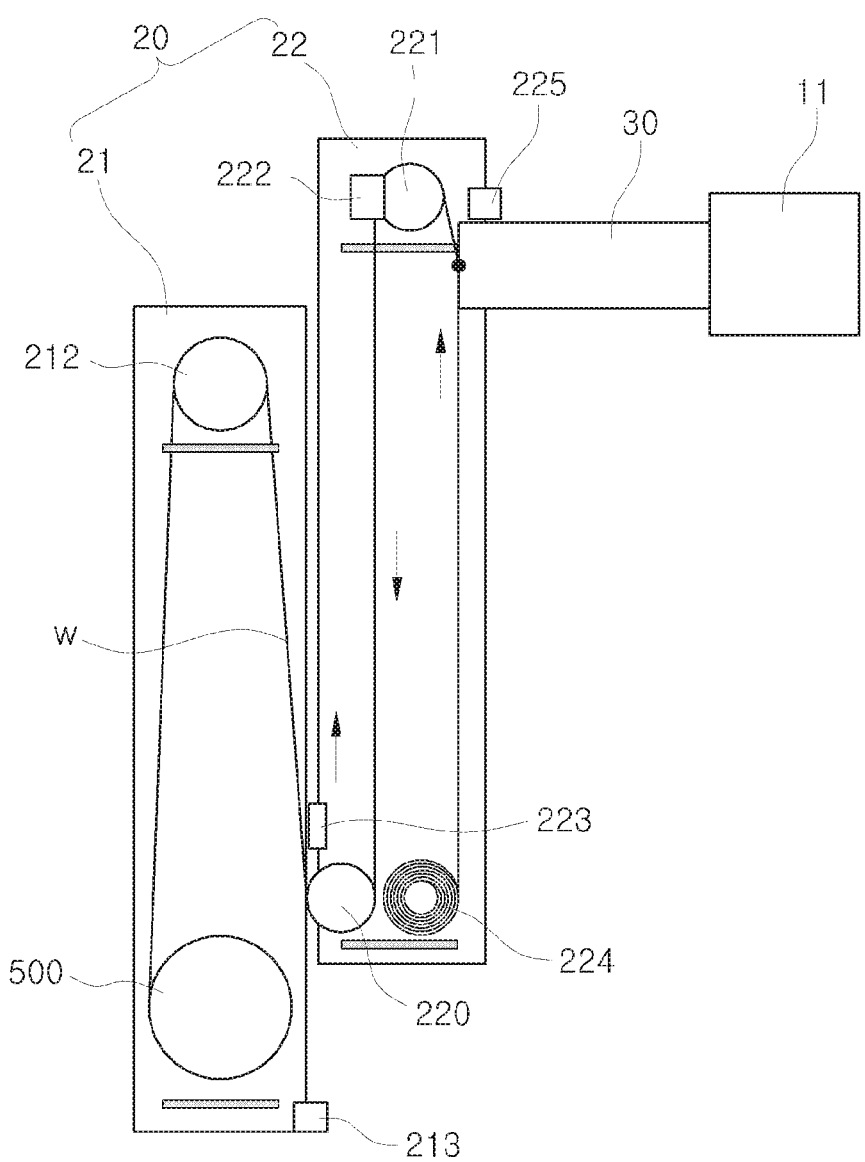
FIGS. 4 and 5 are views illustrating the internal structure of the column according to an embodiment.
Figure 5:
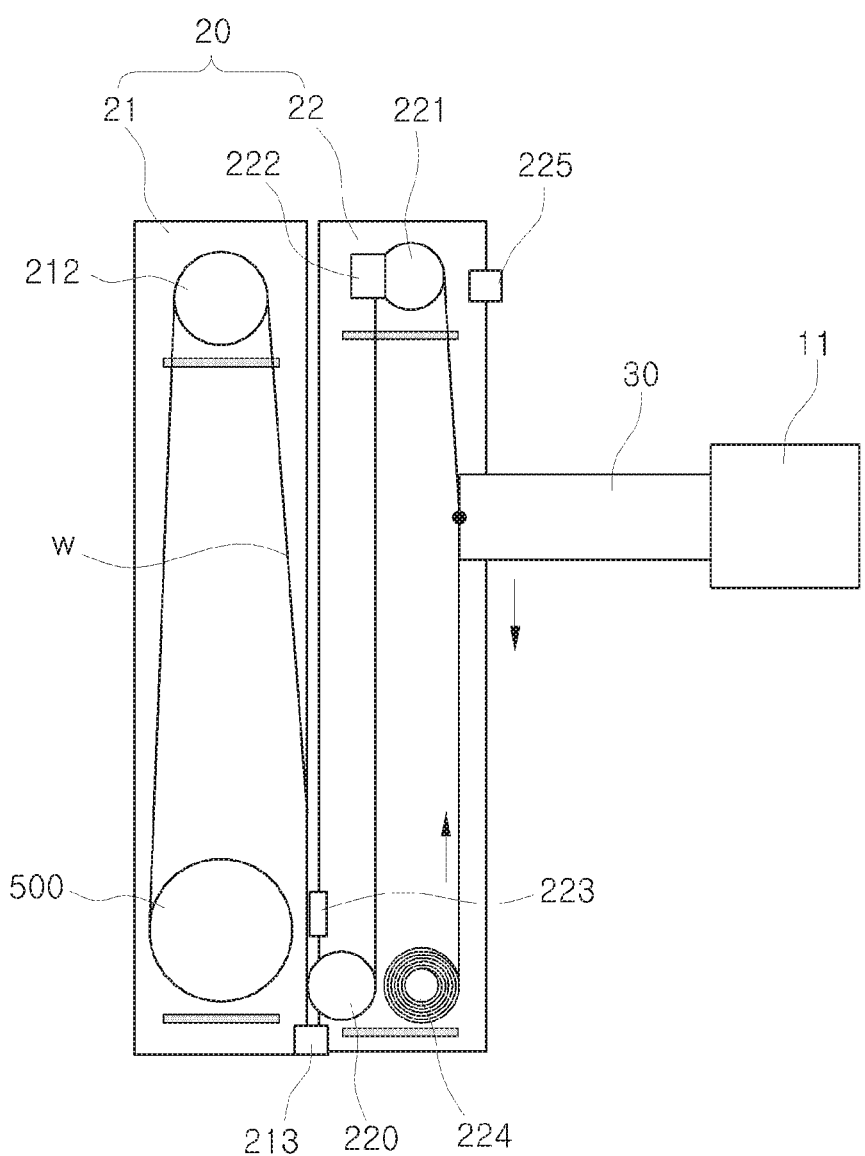

FIGS. 4 and 5 are views illustrating the internal structure of the column according to an embodiment.

Referring to FIGS. 4 and 5, the column 20 according to an embodiment includes the first column 21, the second column 22, and the arm 30 mounted to the second column 22. The X-ray source 11 may be mounted to the arm 30. The first column 21, the second column 22 and the arm 30 may be connected by a single wire w. The user may move the second column 22 and the arm 30 in the vertical direction in a state where the weight of the second column 22, the arm 30 and the X-ray source 11 is compensated by a weight compensator.

The weight compensator may include a spring balancer 500. The spring balancer 500 may be installed to the first column 21. Specifically, the spring balancer 500 may be installed inside the first column 21 to be positioned at a lower portion of the first column 21. However, the position of the spring balancer 500 is not limited to the above example but may be variously changed. For example, the spring balancer 500 may be installed outside the first column 21. The spring balancer 500 may include a pulley and an elastic member. In this case, the elastic member may include a spring in the rolled form of a spiral shape. In this case, the pulley may include a drum pulley.

The weight compensator may further include a guide pulley 212. The guide pulley 212 may be installed to the first column 21. Specifically, the guide pulley 212 may be installed inside the first column 21 to be positioned at an upper portion of the first column 21. In other word, the guide pulley 212 may be installed inside the first column 21 to be positioned at an upper portion of the spring balancer 500. However, the position of the guide pulley 212 is not limited to the above example but may be variously changed. For example, the guide pulley 212 may be installed outside the first column 21. The wire w may be wound on the guide pulley 212. The wire w wound on the guide pulley 212 may be extended to be wound on a third pulley 220 positioned at a lower portion of the second column 22.

The guide pulley 212 is a kind of general pulley, and a conventional pulley may be used. The structural feature of the guide pulley 212 may allow the load of the second column 22 and the arm 30 mounted on the second column 22 to be uniformly supported by a first elastic member (such as an elastic member of the spring balancer 500). The user may slide the second column 22 in a state where the load of the second column 22 and the arm 30 is compensated.

The wire w may be wound on a third pulley 220 positioned at the lower portion of the second column 22 and extended to a fourth pulley 221 positioned at an upper portion of the second column 22. The wire w may be wound on and extended to the fourth pulley 221 and mounted on the arm 30.

A second elastic member 224 may be provided at the lower portion of the second column 22. The second elastic member 224 may be provided in the form of a static-load spring for supporting a uniform load or in the form of a static-torque spring for supporting a uniform torque. One side of the second elastic member 224 may be connected to the arm 30.

The arm 30 may be moved up and down by a uniform force by the second elastic member 224.

When the second column 22 is moved in the vertical direction, the weight compensation structure may compensate the load of the second column 22 and the arm 30. If a state in which the second column 22 is lowered to the lowest position where it can no longer descend is referred to as a parking state, when the arm 30 is moved in the vertical direction in the parking state, the weight compensation structure does not need to support the load of the second column 22.

That is, when the arm 30 is moved in the vertical direction in the state where the second column 32 is parked, the weight compensation structure supports only the load of the arm 30. The weight compensation structure is set to support the load of both the second column 22 and the arm 30, so that a force required when the arm 30 is moved in the vertical direction in the state where the second column 22 is parked may be different from a force required when the arm 30 is moved in the vertical direction in the state where the second column 22 is not parked.

The second elastic member 224 may transmit an elastic force to the arm 30 so that the arm 30 may be supported with a uniform load even when the second column 22 is parked. The second elastic member 224 may provide the arm 30 with an elastic force of the same magnitude as the load of the second column 22 so that the arm 30 may be supported with a uniform load. Accordingly, the arm 30 may be moved by a uniform force regardless of whether or not the second column 22 is parked.

The second elastic member 224 may be extended or shortened as the arm 30 moves in the vertical direction. For example, the second elastic member 224 may be provided in the rolled form of a spiral shape so that when the arm 30 is lifted, the second elastic member 224 may be unrolled and extended, and when the arm 30 is lowered, the unrolled second elastic member 224 may be rolled and shortened.

As such, the weight of the second column 22 and the arm 30 may be compensated by the spring balancer 500, and the arm 30 may be moved up and down by a uniform force generated by the second elastic member 224 provided in the second column 22. The user may manually change the position of the X-ray source 11, and thus the x-ray source 11 may be positioned at a desired position more quickly than when the position of the x-ray source 11 is changed by a driving source.

Further, in comparison with a conventional weight compensator using a heavy weight or the like, the weight compensator of the present disclosure is implemented by mechanisms such as a plurality of pulleys, wires, and elastic members, and thus is light in weight compared to the conventional weight compensator. Therefore, the X-ray imaging apparatus may be lightened and easily moved.

The column 20 may be provided with a column brake 223 for braking the movement of the second column 22 and an arm brake 222 for braking the movement of the arm 30. The column brake 223 and the arm brake 222 may be positioned in the second column 22. The mounting positions of the column brake 223 and the arm brake 222 are not limited to those described above.

The column 20 may be provided with a sensor for sensing the positions of the second column 22 and the arm 30. The sensor may include a first sensor 213 provided on the first column 21 and a second sensor 225 provided on the second column 22.

The first sensor 213 may be positioned at the lower portion of the first column 21 to sense the second column 22. The second sensor 225 may be positioned at the upper portion of the second column 22 to sense the arm 30. The movement of the second column 22 or the arm 30 may be controlled according to the result that the first sensor 213 or the second sensor 225 senses the second column 22 or the arm 30.

Accordingly, the first sensor 213 may be positioned on the lowermost side where the second column 22 may move along the first column 21, and the second sensor 225 may be positioned on the uppermost side where the arm 30 may move along the second column 22.

The X-ray imaging apparatus 1 may be provided with a controller for controlling the movement of the column 20 and the arm 30. The controller may operate the column brake 223 or the arm brake 222 according to the result sensed by the first sensor 213 or the second sensor 225. The column brake 223 and the arm brake 222 may be in an ON state to prevent the second column 22 and the arm 30 from moving in the absence of external force.

For example, the user may manipulate the column brake 223 to be in an OFF state in order to move the X-ray source 11 downward. When the column brake 223 becomes the OFF state, the user may move the second column 22 downward by applying an external force thereto. When the second column 22 moves downward and is sensed by the first sensor 213, the controller turns on the column brake 223. When the column brake 223 is turned on, the second column 22 does not move further downward and stops. When the X-ray source 11 needs to move further downward, the user may move the arm 30 downward in a state where the arm brake 222 is turned off.

In order to move the X-ray source 11 upward, the user may manipulate the arm brake 222 to turn off. When the arm brake 222 is turned off, the user may move the arm 30 upward by applying an external force thereto. When the arm 30 moves upward and is sensed by the second sensor 225, the controller may turn on the arm brake 222. When the arm brake 222 is turned on, the arm 30 does not move further upward and stops. When the X-ray source 11 needs to move further upward, the user may move the second column 22 upward in a state where the column brake 223 is turned off.

Although the case where the second column 22 is moved downward before the movement of the arm 30 in order to move the X-ray source 11 downward and the arm 30 is moved upward before the movement of the second column 22 in order to move the X-ray source 11 upward has been described above, the order of moving the second column 22 or the arm 30 to move the X-ray source 11 downward or upward is not limited to the above description. Also, the control method and installation position of the first sensor 213, the second sensor 225, the column brake 223 and the arm brake 222 are not limited to those described above.

Figure 6:
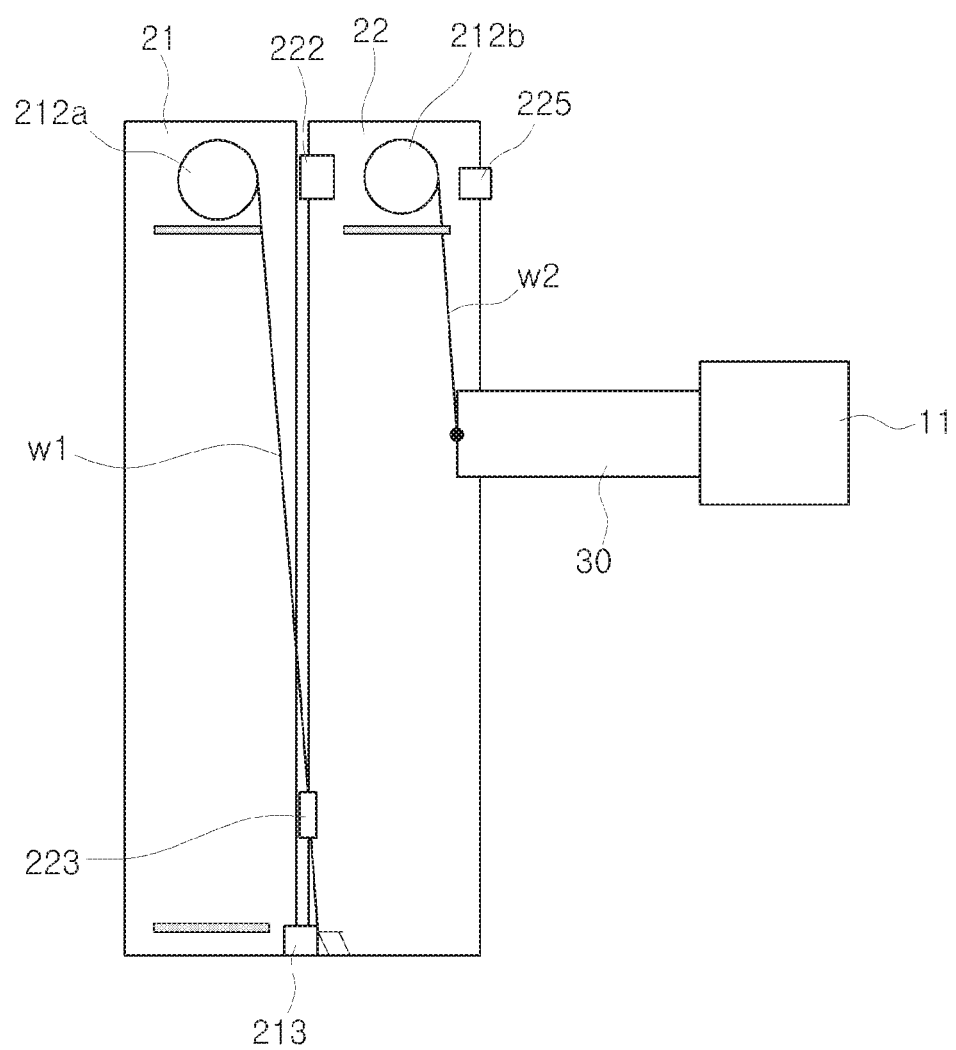
FIG. 6 is a view illustrating the internal structure of a column according to another embodiment.

FIG. 6 is a view illustrating the internal structure of a column according to another embodiment.

Referring to FIG. 6, the column 20 according to another embodiment may include the first column 21, the second column 22 provided to be movable along the first column 21, the arm 30 provided to be movable along the second column 22. The X-ray source 11 may be mounted on the arm 30. The weight of the second column 22 and the arm 30 may be compensated by a plurality of weight compensators.

In the case of FIGS. 4 and 5, the single wire w connects the first column 21, the second column 22, and the arm 30, so that the weight of the second column 22 and the arm 30 may be compensated for by a weight compensator connected in one body as a whole. However, in the case of FIG. 6, the weight of the second column 22 and the arm 30 may be compensated for by a plurality of weight compensators. The plurality of weight compensators may include a first weight compensator and a second weight compensator.

The first column 21 and the second column 22 may each be provided with a weight compensator of a similar structure. The weight of the second column 22 and the arm 30 may be compensated for by the first weight compensator positioned in the first column 21, and the weight of the arm 30 may be compensated for by the second weight compensator positioned in the second column 22. The positions of the first weight compensator and the second weight compensator are not limited to the above-described example but may be variously changed. For example, the first weight compensator and the second weight compensator may be installed outside the first column 21 and the second column 22, respectively.

The first weight compensator may include a first spring balancer 212*a*. The first spring balancer 212*a* may be installed to the first column 21. Specifically, the first spring balancer 212*a* may be installed inside the first column 21 to be positioned at the upper portion of the first column 21. However, the position of the first spring balancer 212*a* is not limited to the above example but may be variously changed. As an example, the first spring balances 212*a* may be provided outside the first column 21. A first wire w1 may be wound on the first spring balancer 212*a*. The first wire w1 may be wound on and pass through the first spring balancer 212*a* to be fixed to the second column 22. That is, one side of the first wire w1 may be fixed to the first spring balancer 212*a* and the other side may be fixed to the second column 22.

The first spring balancer 212*a* may have a structure similar to that of the second elastic member 224 illustrated in FIGS. 4 and 5. The first spring balancer 212*a* may support the load of the second column 22 and the arm 30 transmitted through the first wire w1. The user may move the second column 22 in the vertical direction in a state where the load of the second column 22 and the arm 30 is compensated for by the first spring balancer 12*a*.

The second column 22 may be provided with the second weight compensator similar to the first weight compensator.

The second weight compensator may include a second spring balancer 212*b* similar to the first spring balancer 212*a*. The second spring balancer 212*b* may be installed to the second column 22. Specifically, the second spring balancer 212*b* may be installed inside the second column 22 to be positioned at the upper portion of the second column 22. However, the position of the second spring balancer 212*b* is not limited to the above example but may be variously changed. As an example, the second spring balancer 212*b* may be installed outside the second column 22. A second wire w2 may be wound on the first spring balancer 212*a*. The first wire w1 may be wound on and pass through the second spring balancer 212*b* to be fixed to the arm 30. That is, one side of the second wire w2 may be fixed to the second spring balancer 212*b* and the other side may be fixed to the arm 30.

The second spring balancer 212*b* may support the load of the arm 30 transmitted through the second wire w2. The user may move the arm 30 in the vertical direction in a state where the load of the arm 30 is compensated for by the second spring balancer 212*b*.

The structures and functions of the column brake 223, the arm brake 222, the first sensor 213 and the second sensor 225 illustrated in FIG. 6 are similar to structures and functions described for the column brake 223, the arm brake 222, the first sensor 213 and the second sensor 225 illustrated in FIGS. 4 and 5.

Although the weight compensator in FIG. 6 is slightly difference from the weight compensator in FIGS. 4 and 5 in that separate weight compensators are provided in the first column 21 and the second column 22, respectively, both are similar in that the position of the X-ray source may be quickly changed manually.

Figure 7:
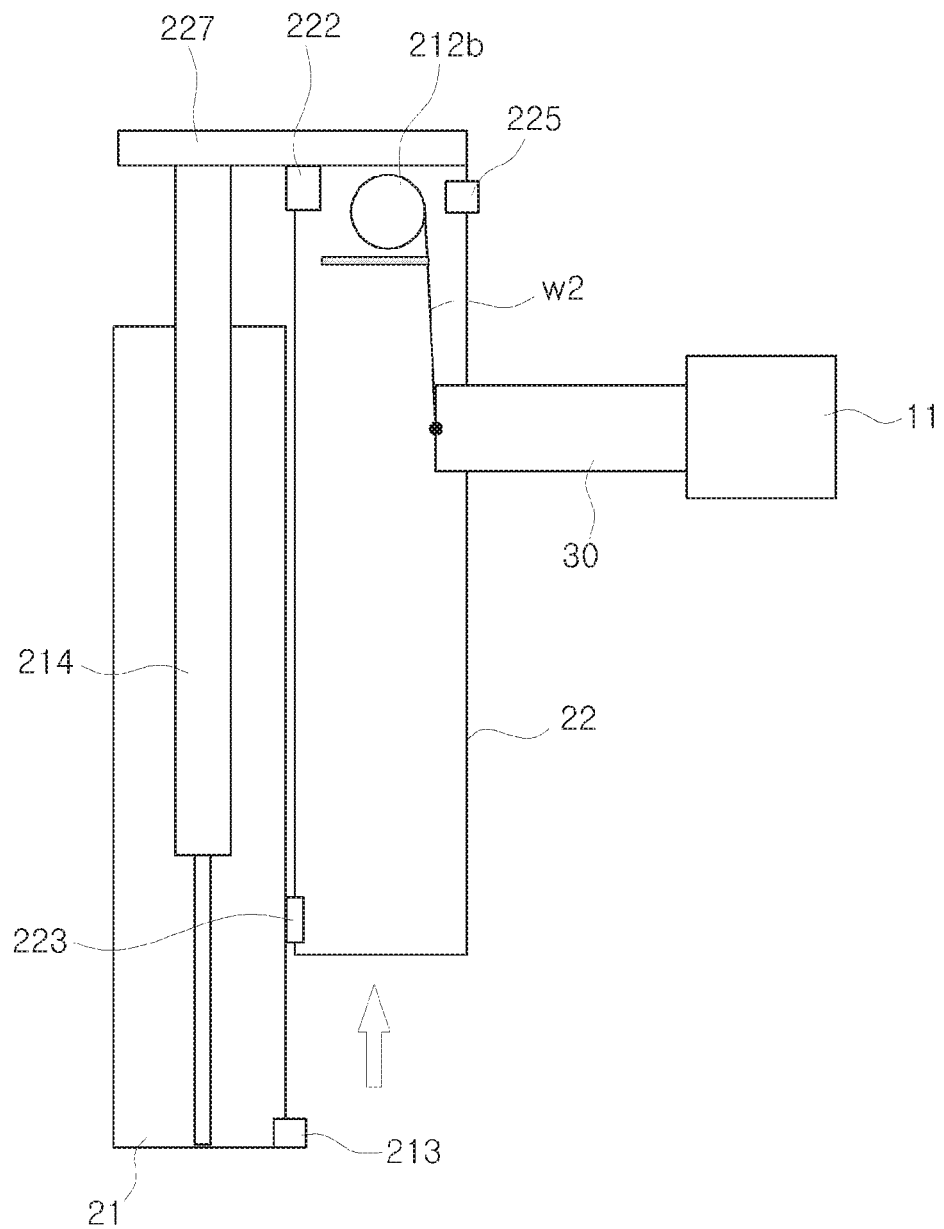
FIGS. 7 and 8 are views illustrating the internal structure of a column according to another embodiment.
Figure 8:
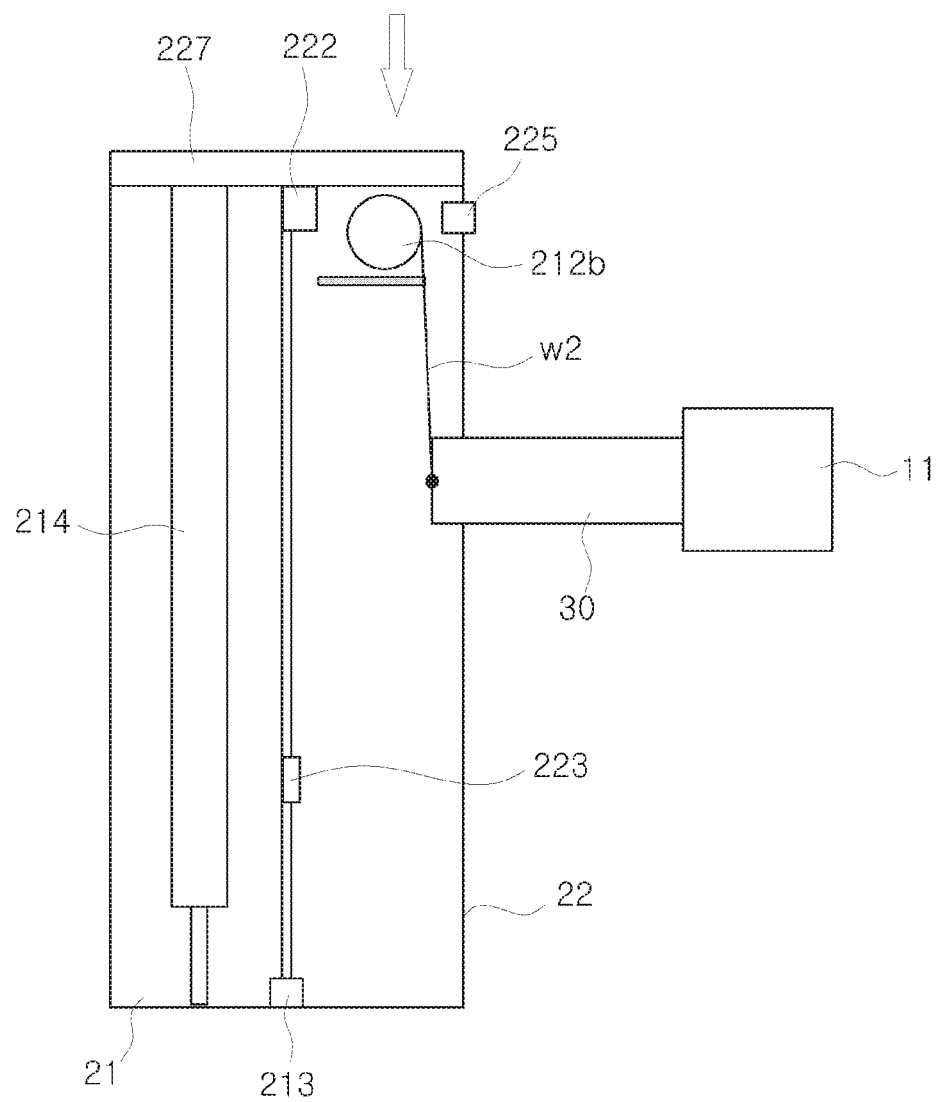

FIGS. 7 and 8 are views illustrating the internal structure of a column according to another embodiment.

Referring to FIGS. 7 and 8, the column 20 according to another embodiment may include the first column 21 and the second column 22, and separate weight compensators may be provided in the first column 21 and the second column 22, respectively. The weight of the second column 22 and the arm 30 mounted on the second column 22 may be compensated for by the weight compensator provided in the first column 21. The weight of the arm 30 may be compensated for by the weight compensator provided in the second column 22.

The first column 21 may be provided with a hydraulic spring 214 for supporting the load of the second column 22 and the arm 30. The second column 22 may be provided a support 227 that may be supported by the hydraulic spring 214. The support 227 may be positioned on the upper portion of the second column 22 and extend from the second column 22 toward the first column 21. The hydraulic spring 214 may support the bottom surface of the support 227. The load of the second column 22 and the arm 30 may be compensated for by a force with which the hydraulic spring 214 presses the bottom surface of the support 227.

The configuration in which the hydraulic spring 214 may support the second column 22 is not limited to the configuration of the support 227 but may be implemented in various structures.

The second column 22 may be provided with the weight compensator provided in the second column 22 illustrated in FIG. 6.

The weight compensator may include the second spring balancer 212b. The second spring balancer 212b may be installed to the second column 22. Specifically, the second spring balancer 212b may be installed inside the second column 22 to be positioned at the upper portion of the second column 22. However, the position of the second spring balancer 212b is not limited to the above example but may be variously changed. As an example, the second spring balancer 212b may be installed outside the second column 22. One side of the second wire w2 may be fixed to and wound on the second spring balancer 212b and the other side may be fixed to the arm 30.

The second spring balancer 212b may support the load of the arm 30 transmitted through the second wire w2. The user may move the arm 30 in the vertical direction in a state e the load of the arm 30 is compensated for by the second spring balancer 212b.

The structures and functions of the column brake 3, the arm brake 222, the first sensor 213 and the second sensor 225 illustrated in FIGS. 7 and 8 are similar to structures and functions described for the column brake 223, the arm brake 222, the first sensor 213 and the second sensor 225 illustrated in FIGS. 4 and 5.

As such, the first column 21 and the second column 22 according to another embodiment of the present disclosure may be provided with separate weight compensators, respectively. Although the above embodiment has described that the first column 21 is provided with the hydraulic spring 214 and the second column 22 is provided with the weight compensator including the pulley and the wire, the second column 22 may be provided with the hydraulic spring 214 and the first column 21 may be provided with the first weight compensator illustrated in FIG. 6.

The weight compensator provided in the X-ray imaging apparatus according to another embodiment of the present disclosure is advantageous in that the position of the x-ray source may be quickly changed manually and it may be implemented as a light weight compensator including a hydraulic spring, a pulley, a wire, and the like.

Figure 9:
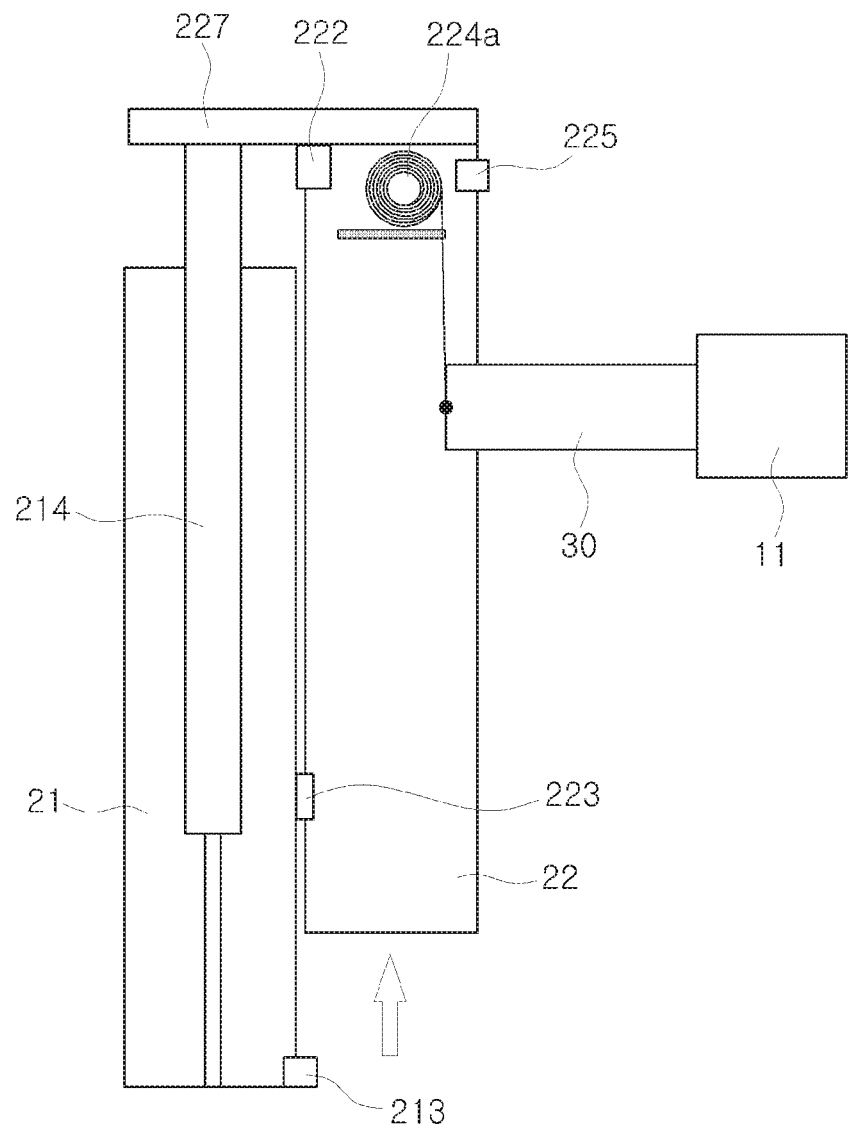
FIGS. 9 and 10 are views illustrating the internal structure of a column according to another embodiment.
Figure 10:
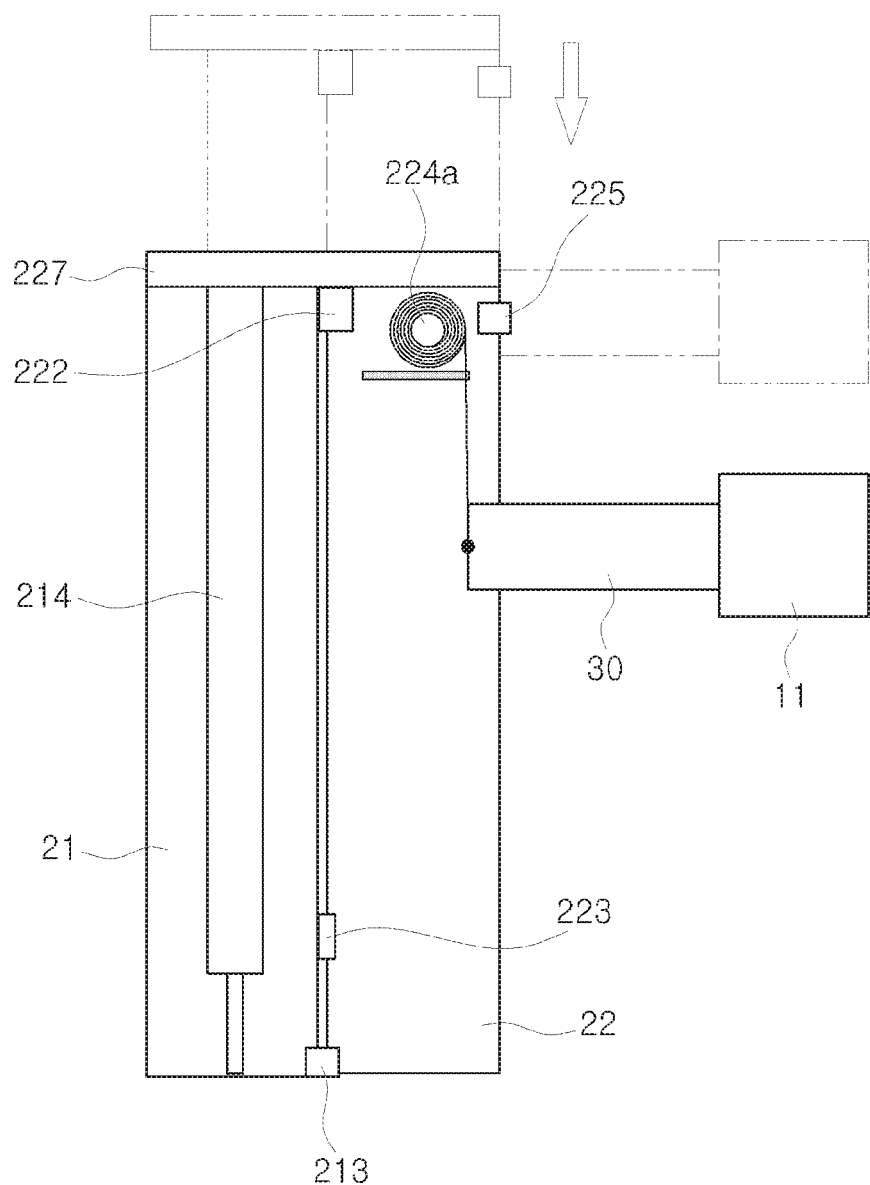

FIGS. 9 and 10 are views illustrating the internal structure of a column according to another embodiment.

Referring to FIGS. 9 and 10, the first column 21 and the second column 22 of the column 20 according to another embodiment may be provided with separate weight compensators, respectively. The weight of the second column 22 and the arm 30 may be compensated for by the weight compensator provided in the first column 21, and the weight of the arm 30 may be compensated for by the weight compensator provided in the second column 22.

The first column 21 may be provided with the hydraulic spring 214 as in the first column 21 illustrated in FIGS. 7 and 8. The second column 22 is provided with the support 227 extending toward the first column 21 and the hydraulic spring 214 may support the support 227. The load of the second column 22 and the arm 30 may be compensated for by a force with which the hydraulic spring 214 presses the bottom surface of the support 227.

The second column 22 may be provided with a fifth elastic member 224a. The fifth elastic member 224a may be provided in the form of a static-load spring for supporting a uniform load or in the form of a static-torque spring for supporting a uniform torque. The fifth elastic member 224a may be positioned at the upper portion of the second column 22.

One side of the fifth elastic member 224a may be connected to the arm 30. The fifth elastic member 224a may be shortened or extended as the arm 30 is lifted or lowered. For example, the fifth elastic member 224a may be provided in the rolled form of a spiral shape. When the arm 30 is lowered, the fifth elastic member 224a may be unrolled and extended, and when the arm 30 is lifted, fifth elastic member 224a may be rolled so that the length extending from the fifth elastic member 224a to the arm 30 may be shortened.

The load of the arm 30 may be compensated for by the fifth elastic member 224a. The user may move the arm 30 in the vertical direction in a state where the load of the arm 30 and the X-ray source mounted on the arm 30 is compensated for by the fifth elastic member 224a.

The structures and functions of the column brake 223, the arm brake 222, the first sensor 213 and the second sensor 225 illustrated in FIGS. 9 and 10 are similar to structures and functions described for the column brake 223, the arm brake 222, the first sensor 213 and the second sensor 225 illustrated in FIGS. 4 and 5.

Figure 11:
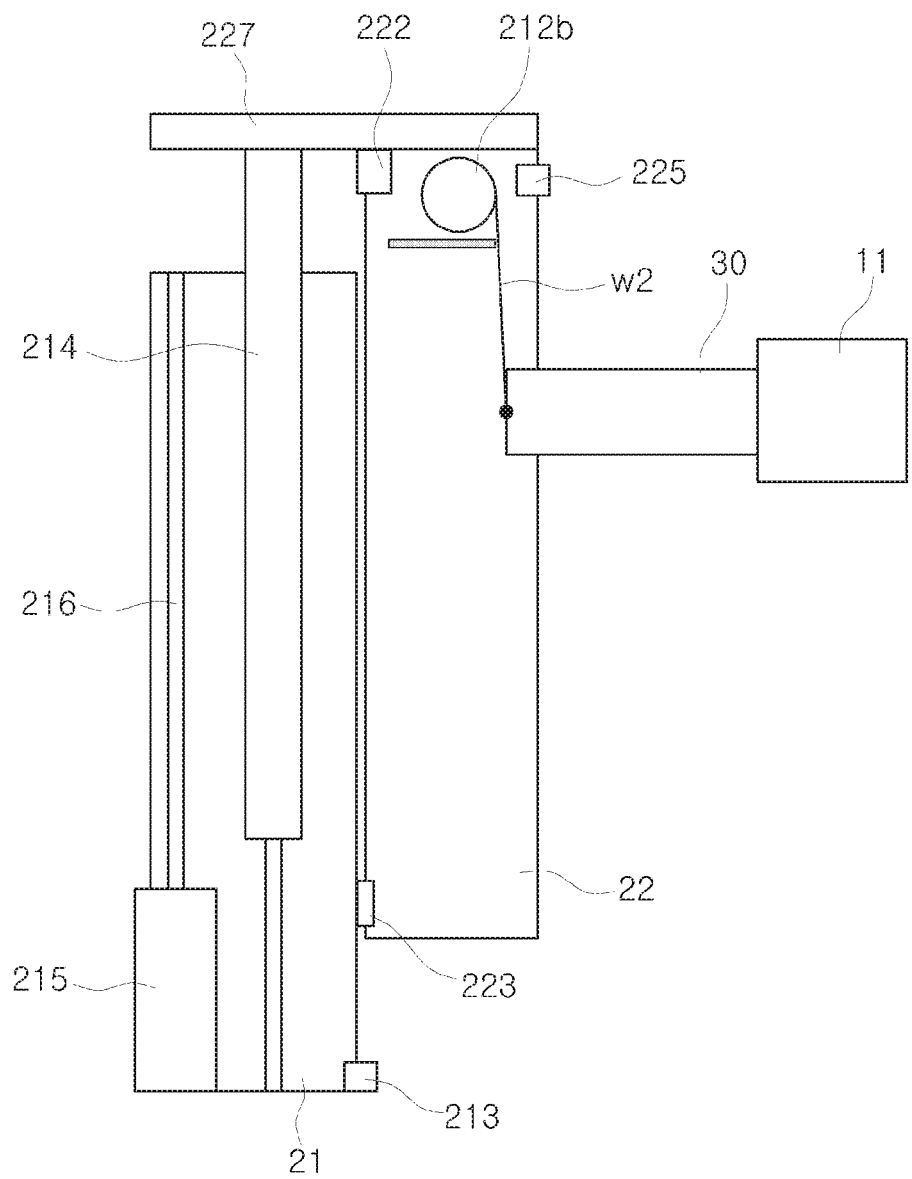
FIG. 11 is a view illustrating the internal structure of a column according to another embodiment.

FIG. 11 is a view illustrating the internal structure of a column according to another embodiment.

Referring to FIG. 11, the column 20 according to another embodiment includes the first column 21, the second column 22 provided to be movable in the vertical direction along the first column 21, and the arm 30 provided to be movable in the vertical direction along the second column 22. The X-ray source 11 may be mounted on the arm 30.

The first column 21 and the second column 22 may be provided with separate weight compensators, respectively. The weight of the second column 22 and the arm 30 mounted on the second column 22 may be compensated for by the weight compensator provided in the first column 21. The weight of the arm 30 may be compensated for by the weight compensator provided in the second column 22.

When the second column 22 moves along the first column 21, the weight of the second column 22 and the arm 30 may be automatically compensated for by the driving source 215 provided in the first column 21. When the arm 30 moves along the second column 22, the weight of the arm 30 may be compensated for by the weight compensator having a mechanical structure.

The first column 21 may be provided with the hydraulic spring 214 for supporting the load of the second column 22 and the arm 30. The second column may be provided with the support 227 that may be supported by the hydraulic spring 214. The second column 22 may be provided with the support 227 that may be supported by the hydraulic spring 214.

For example, the support 227 may be positioned at the upper portion of the second column 22 and extend from the second column 22 toward the first column 21 so that the bottom surface thereof may be supported by the hydraulic spring 214. The load of the second column 22 and the arm 30 may be compensated for by a force with which the hydraulic spring 214 supports the second column 22.

The weight of the second column 22 and the arm 30 is compensated for by the hydraulic spring 214 so that the user may move the second column 22 in the vertical direction with a small force. When the second column 22 moves upward, the hydraulic spring 214 may be extended, and when the second column 22 moves downward, the hydraulic spring 214 may be compressed.

The hydraulic spring 214 provides an elastic force by a force that the fluid contained therein compresses or expands, and the force when compressing and the force when expanding may not coincide exactly with each other. Therefore, when the second column 22 moves upward or downward, the magnitude of the force compensated for by the hydraulic spring 214 may not be constant.

The first column 21 may be provided with a driving source 215 to compensate for the varying magnitude of the force compensated for by the hydraulic spring 214. The driving source 215 and the second column 22 side may be connected by a connector 216. As an example, the connector 216 may be mounted to the driving source 215 and the support 227 extending from the second column 22. The second column 22 may be moved upward or downward automatically by receiving a driving force from the driving source 215 through the connector 216.

When the driving source 215 is provided solely, a driving source having a large output is required to generate a driving force for compensating for the load of the second column 22 and the arm 30. Therefore, the size and weight of the driving source may be increased. However, because the hydraulic spring 214 is provided together with the driving source 215, the size and weight of the driving source 215 that provides the driving force required to compensate for the load of the second column 22 and the arm 30 may be reduced.

The connector 216 may be composed of a plurality of pulleys, belts, and the like.

The second column may be provided with a weight compensator similar to the second weight compensator illustrated in FIG. 6.

The weight compensator may include the second spring balancer 212b. The second spring balancer 212b may be installed to the second column 22. Specifically, the second spring balancer 212b may be installed inside the second column 22 to be positioned at the upper portion of the second column 22. However, the position of the second spring balancer 212b is not limited to the above example but may be variously changed. As an example, the second spring balancer 212b may be installed outside the second column 22. One side of the second wire w2 may be fixed to the second spring balancer 212b to be wound on the second spring balancer 212b and the other side may be fixed to the arm 30.

The second spring balancer 212b may support the load of the arm 30 transmitted through the second wire w2. The user may manually move the arm 30 in the vertical direction in a state where the load of the arm 30 is compensated for by the second spring balancer 212b.

As such, the second column 22 may be automatically moved in the vertical direction by the driving source 215 and the arm 30 may be manually moved in the vertical direction.

Figure 12:
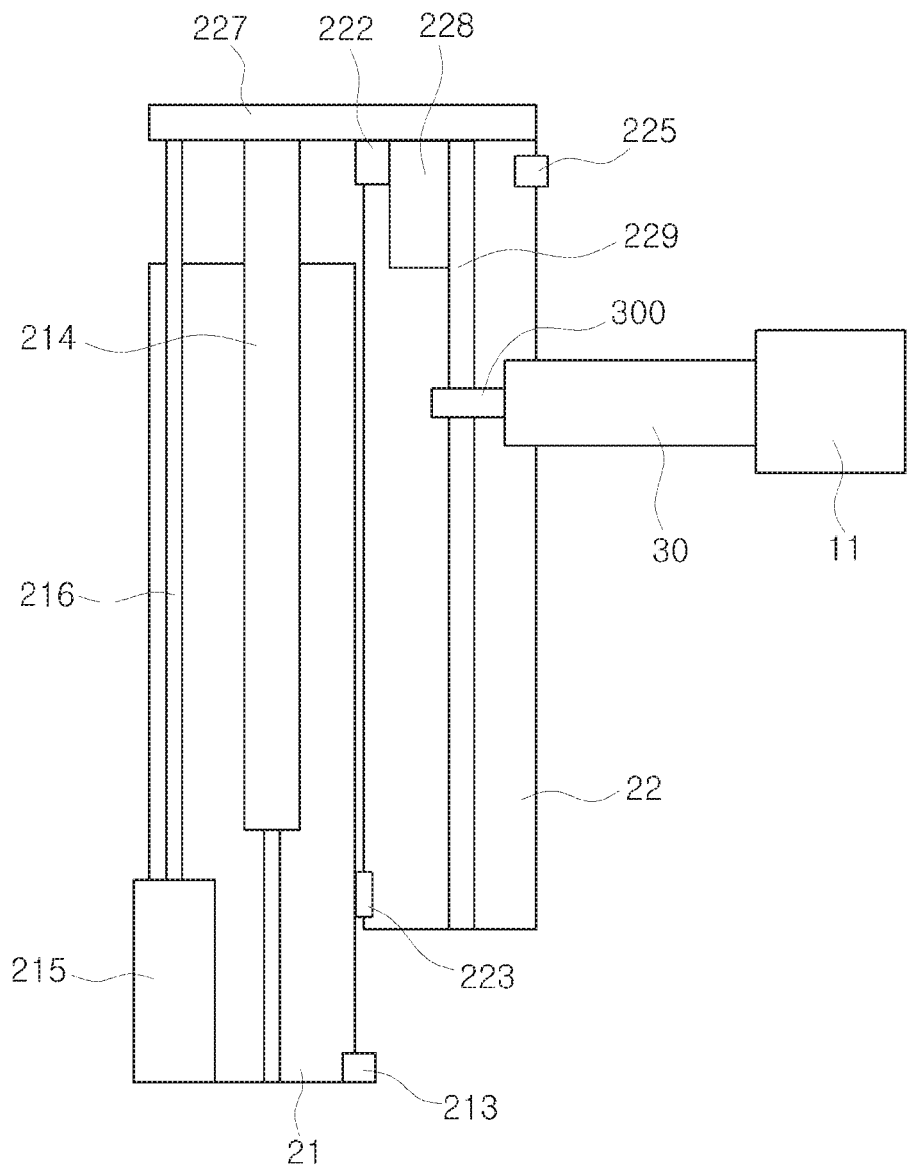
FIG. 12 is a view illustrating the internal structure of a column according to another embodiment.

FIG. 12 is a view illustrating the internal structure of a column according to another embodiment.

Referring to FIG. 12, the column 20 according to another embodiment may include the first column 21, the second column 22 provided to be movable in the vertical direction along the first column 21, and the arm 30 provided to be movable in the vertical direction along the second column 22. The X-ray source 11 may be mounted on the arm 30.

The first column 21 may be provided with both the hydraulic spring 214 and the driving source 215 as in the first column 21 illustrated in FIG. 11. When the second column 22 moves upward or downward along the first column 21, the weight of the second column 22 and the arm 30 may be automatically compensated for by the driving source 215. The contents about the hydraulic spring 214 and the driving source 215 illustrated in FIG. 11 may be similarly applied to the hydraulic spring 214 and the driving source 215 illustrated in FIG. 12.

Because the hydraulic spring 214 is provided together with the driving source 215, the size and weight of the driving source 215 for compensating for the load of the second column 22 and the arm 30 may be reduced.

The second column 22 may be provided with a separate driving source 228 for compensating for the load of the arm 30. A ball screw 229 extending in the longitudinal direction of the second column 22, that is, the vertical direction, may be provided inside the second column 22. The ball screw 229 may be connected to the driving source 228 to be rotated by receiving a driving force from the driving source 228.

A nut portion 300 may be connected to the arm 30. The nut portion 300 may be mounted on the ball screw 229 to move upward or downward as the ball screw 229 rotates. The arm 30 may be provided to be movable upward or downward along the ball screw 229 together with the nut portion 300.

The arm 30 may be automatically moved upward or downward by the configuration of the ball screw 229 and the nut portion 300, or the weight of the arm 30 is automatically compensated for by the configuration of the ball screw 229 and the nut portion 300 connected to the driving source 228, and the upward and downward movement of the arm 30 may be manually performed by the user.

The embodiments in which a weight compensator includes a pulley, a wire and an elastic member, a weight compensator includes a hydraulic spring, and a weight compensator includes a driving source are described above. The first column 21 and the second column 22 may be provided with the weight compensators having the same structure, respectively, or may be provided with the weight compensators having a different structure, respectively. The combination of the weight compensators provided in the first column 21 and the second column 22 is not limited to that described above.

The weight compensator may further include a pulley unit (not shown) on which the wire is wound. The pulley unit may include at least one of a first pulley provided to be fixed and a second pulley provided to be movable. More than one of the first pulley may be provided. More than one of the second pulley may also be provided.

In the weight compensator including a pulley, a wire and an elastic member, not only a spring in the rolled form of a spiral shape but also a tension spring, a compression spring and the like may be used as the elastic member.

The spring balancer may be provided to have the same diameter or different diameters. As an example having different diameters, the spring balancer may be provided in such a manner that the diameter of the center portion thereof is larger than the diameter of opposite end portions thereof.

In the above description, the weight compensator is provided in the column provided in the X-ray imaging apparatus. However, the present disclosure is not limited to the X-ray imaging apparatus but may be applied to any apparatus requiring a weight compensator.

The invention claimed is:

1. An X-ray imaging apparatus comprising:
   a first column connected to a main body;
   a second column connected to the first column and provided to be movable relative to the first column;
   an arm, on which an X-ray source is mountable, connected to the second column and slidably provided along the second column;
   a spring balancer in the first column;
   a spring in the second column; and
   a wire having a first end connected to the spring balancer and a second end connected to the spring, and being connected to the arm between the first and second ends, so that the spring balancer, the spring and the wire are configured to allow the arm to be manually moved by a uniform force regardless of a position of the second column.

2. The X-ray imaging apparatus according to claim 1, wherein the spring is a static-load elastic member.

3. The X-ray imaging apparatus according to claim 1, wherein the spring is a static-torque elastic member.

4. The X-ray imaging apparatus according to claim 1, further comprising:
   a guide pulley to which the wire is connected,
   wherein the spring balancer compensates for a load of the second column and the arm with a uniform force by the guide pulley.

5. The X-ray imaging apparatus according to claim 1, further comprising:
   a column brake to brake movement of the second column.

6. The X-ray imaging apparatus according to claim 1, further comprising:
   an arm brake to brake movement of the arm.

7. The X-ray imaging apparatus according to claim 1, further comprising:
   a first sensor to sense a position of the second column.

8. The X-ray imaging apparatus according to claim 7, wherein
   the first sensor is provided to sense the position of the second column when the second column is located at a lowermost portion to which the second column is movable at the lowermost in the first column.

9. The X-ray imaging apparatus according to claim 1, further comprising:
   a second sensor to sense a position of the arm.

10. The X-ray imaging apparatus according to claim 9, wherein the second sensor is provided to sense the position of the arm when the arm is located at an uppermost portion to which the second arm is movable at the uppermost in the second column.

* * * * *